(12) United States Patent
Kolstad

(10) Patent No.: US 8,361,384 B1
(45) Date of Patent: Jan. 29, 2013

(54) WATER TREATMENT DEVICE AND METHODS OF USE

(75) Inventor: David Kolstad, Denver, CO (US)

(73) Assignee: Aardvark IP Holding, LLC, Denver, CO (US)

( * ) Notice: Subject to any disclaimer, the term of this patent is extended or adjusted under 35 U.S.C. 154(b) by 720 days.

(21) Appl. No.: 12/534,761

(22) Filed: Aug. 3, 2009

Related U.S. Application Data

(60) Provisional application No. 61/085,419, filed on Aug. 1, 2008.

(51) Int. Cl.
- *A61L 2/00* (2006.01)
- *G01N 21/00* (2006.01)
- *A61N 5/00* (2006.01)

(52) U.S. Cl. ............ 422/24; 422/905; 250/455.11; 250/492.1; 210/748.01; 210/748.03; 210/748.1; 210/748.11

(58) Field of Classification Search ............ 422/24, 422/905; 250/455.11, 492.1; 210/748.01, 210/748.03, 748.1, 748.11
See application file for complete search history.

(56) References Cited

U.S. PATENT DOCUMENTS

| | | | |
|---|---|---|---|
| 4,141,830 A | 2/1979 | Last | |
| 4,207,286 A | 6/1980 | Gut Boucher | |
| 4,220,529 A | 9/1980 | Daude-Lagrave | |
| 4,230,571 A | 10/1980 | Dadd | |
| 4,458,153 A | 7/1984 | Wesley | |
| 4,524,079 A | 6/1985 | Hofmann | |
| 4,562,014 A | 12/1985 | Johnson | |
| 4,655,933 A | 4/1987 | Johnson et al. | |
| 4,836,929 A | 6/1989 | Baumann | |
| 4,857,204 A * | 8/1989 | Joklik | 210/695 |
| 4,906,387 A | 3/1990 | Pisani | |
| 5,130,032 A | 7/1992 | Sartori | |
| 5,145,585 A * | 9/1992 | Coke | 210/695 |
| 5,207,921 A | 5/1993 | Vincent | |
| 5,217,607 A | 6/1993 | Dalton, III | |
| 5,419,816 A | 5/1995 | Sampson | |
| 5,424,032 A | 6/1995 | Christensen | |
| 5,556,958 A | 9/1996 | Carroll | |
| 5,595,666 A | 1/1997 | Kochen | |
| 5,662,803 A | 9/1997 | Young | |
| 5,665,762 A | 9/1997 | Carroll | |
| 5,685,994 A * | 11/1997 | Johnson | 210/748.1 |
| 5,750,072 A | 5/1998 | Sangster | |
| 5,753,106 A | 5/1998 | Schenck | |
| 5,780,860 A | 7/1998 | Gadgil | |
| 5,871,620 A | 2/1999 | Haug | |
| 5,879,546 A | 3/1999 | Burford | |
| 5,997,812 A | 12/1999 | Burnham | |
| 6,090,294 A | 7/2000 | Teran | |

(Continued)

FOREIGN PATENT DOCUMENTS

WO 96/22944 A1 8/1996

OTHER PUBLICATIONS

International Search Report and Written Opinion for International Application No. PCT/US2012/033097, mailed Jun. 29, 2012, 13 pages.

*Primary Examiner* — Jill Warden
*Assistant Examiner* — Monzer Chorbaji
(74) *Attorney, Agent, or Firm* — Sheridan Ross, P.C.

(57) ABSTRACT

A water treatment device and methods of treating cooling tower water are described. The water treatment device utilizes ultraviolet radiation, a magnetic field, and ozone fortified air to treat cooling tower water, resulting in reduced microbial contamination and reduced alkalinity in cooling tower water. Cooling tower water may consequently be run at higher cycles of concentration while reducing or eliminating deposition of minerals on cooling tower components.

22 Claims, 4 Drawing Sheets

U.S. PATENT DOCUMENTS

| | | | |
|---|---|---|---|
| 6,117,335 | A | 9/2000 | Bender |
| 6,419,821 | B1 | 7/2002 | Gadgil |
| 6,468,433 | B1 | 10/2002 | Tribelski |
| 6,469,308 | B1 | 10/2002 | Reed |
| 6,673,248 | B2 | 1/2004 | Chowdhury |
| 6,682,697 | B2 | 1/2004 | He |
| 6,730,205 | B2 | 5/2004 | Holland |
| 6,780,328 | B1 | 8/2004 | Zhang |
| 6,863,826 | B2 | 3/2005 | Sheets |
| 6,986,867 | B2 | 1/2006 | Hanley |
| 6,991,735 | B2 | 1/2006 | Martin |
| 7,118,852 | B2 | 10/2006 | Purdum |
| 7,267,778 | B2 | 9/2007 | de Meulenaer |
| 7,285,223 | B2 | 10/2007 | Martin |
| 7,481,924 | B2 * | 1/2009 | Takahashi et al. ............ 210/222 |
| 7,531,096 | B2 | 5/2009 | Yarbrough |
| 2002/0139750 | A1 | 10/2002 | Boyce |
| 2002/0170816 | A1 | 11/2002 | Leffler |
| 2003/0141260 | A1 | 7/2003 | Corbin |
| 2004/0052680 | A1 | 3/2004 | Elwood |
| 2004/0055965 | A1 | 3/2004 | Hubig |
| 2006/0011558 | A1 | 1/2006 | Fencl |
| 2006/0045796 | A1 | 3/2006 | Anderle |
| 2006/0263441 | A1 | 11/2006 | Fukui |
| 2007/0009421 | A1 | 1/2007 | Kittrell et al. |
| 2007/0029261 | A1 | 2/2007 | Chew |
| 2007/0062883 | A1 | 3/2007 | Frederick, Jr. et al. |
| 2007/0125719 | A1 | 6/2007 | Yarbrough |
| 2008/0142452 | A1 | 6/2008 | Denkewica |
| 2010/0219136 | A1 | 9/2010 | Campbell |
| 2011/0024361 | A1 | 2/2011 | Schwartzel |

* cited by examiner

WATER TREATMENT DEVICE AND METHODS OF USE

This application claims priority to and incorporates by reference, U.S. provisional Patent Application No. 61085419, filed 1 Aug. 2008, having the same title and inventor as the present application.

FIELD OF THE INVENTION

The present invention pertains generally to devices and methods for disinfecting, de-alkalinizing, and conditioning water, especially water used in cooling towers for chillers, refrigeration units, condensers, heat exchangers, and similar cooling devices.

BACKGROUND

Water treatment is required to generate or maintain acceptable water quality in systems such as cooling towers, evaporative coolers, heat exchangers, chillers, process recirculation systems, point-of-entry water treatment systems, and various wastewater treatment systems. For instance, many air conditioners and other processes that produce heat as a byproduct or waste product utilize cooling towers to dissipate or dispose of heat. Cooling towers often use water as a cooling medium to absorb heat from air conditioning coils or similar heat dumping devices. Water makes an excellent cooling medium due to its relatively high specific heat capacity, its excellent heat conduction in liquid form, and its relatively high heat of vaporization. However, cooling tower water requires extensive treatment to prevent water quality from degrading to unacceptable levels.

Cooling towers that circulate water to dissipate or dispose of heat usually lose substantial quantities of water to evaporation. A typical air conditioning cooling tower loses to evaporation about 3 gallons per minute of water, per 100 tons of air conditioning capacity. A large hospital may have about 1000 tons of air conditioning capacity. Thus the large hospital air conditioning cooling tower loses about 1800 gallons of water per hour through evaporation. Vaporization of cooling tower water leaves behind substantially all of the solids dissolved in the water that becomes vaporized, resulting in increased concentration of dissolved solids in cooling tower water that remains in liquid phase in the tower. Cooling tower water that is hyper-concentrated with solutes (solute laden) results, and precipitation or deposition of those solids on cooling tower components is a major problem. Cycle(s) of concentration ("cycle") is a measure of the degree to which dissolved solids concentration in circulating water is increased over that of feed water (also referred to as raw water) as follows: feed water is at 1 cycle of concentration; where dissolved solids in circulating water reach a concentration that is twice that of the feed water, the circulating water is at or has undergone 2 cycles of concentration; at a concentration of 4 times that of feed water, the circulating water is at or has undergone 4 cycles of concentration, etc.

Carbonate precipitation and deposition is typically problematic in cooling towers, due at least in part to hyper-concentration of solutes, and to alkalinization. Calcium carbonate and magnesium carbonate are frequently the most problematic species. Carbonate precipitation is exacerbated by highly alkaline cooling tower water because proportions of carbonate to bicarbonate increase with increase in pH, and carbonate is less soluble in water than bicarbonate. Accordingly, precipitation of carbonate is more problematic at higher pH. Control of alkalinity (i.e. lowering pH) is therefore highly desirable in cooling tower water treatment. Bacterial growth and growth of microorganisms or other organisms in cooling tower water and on cooling tower components is also a substantial problem.

Cooling tower water alkalinity and hyper-concentration of dissolved solids is typically addressed by adding chemicals to the water that help keep the dissolved solids in solution or suspension. However, such chemicals can add substantially to building cooling costs. Chemicals (biocides) are also used to inhibit organism growth, but such chemicals can also be costly, and some biocides are less effective under conditions of increased alkalinity.

Cooling tower water quality is also typically maintained by draining a portion of the water (referred to as bleeding off) and replacing the drained water with feed water that is not hyper-concentrated or substantially biologically contaminated by elevated microorganism levels. Use of chemicals to treat cooling tower water can complicate bleeding off, or limit use of some chemicals, because some chemically treated water may require specialized disposal. Ultraviolet (UV) radiation can be effective as a disinfecting agent, but generally does not help with hyper-concentration and deposition of water borne solids.

DETAILED DESCRIPTION

Figure 1:
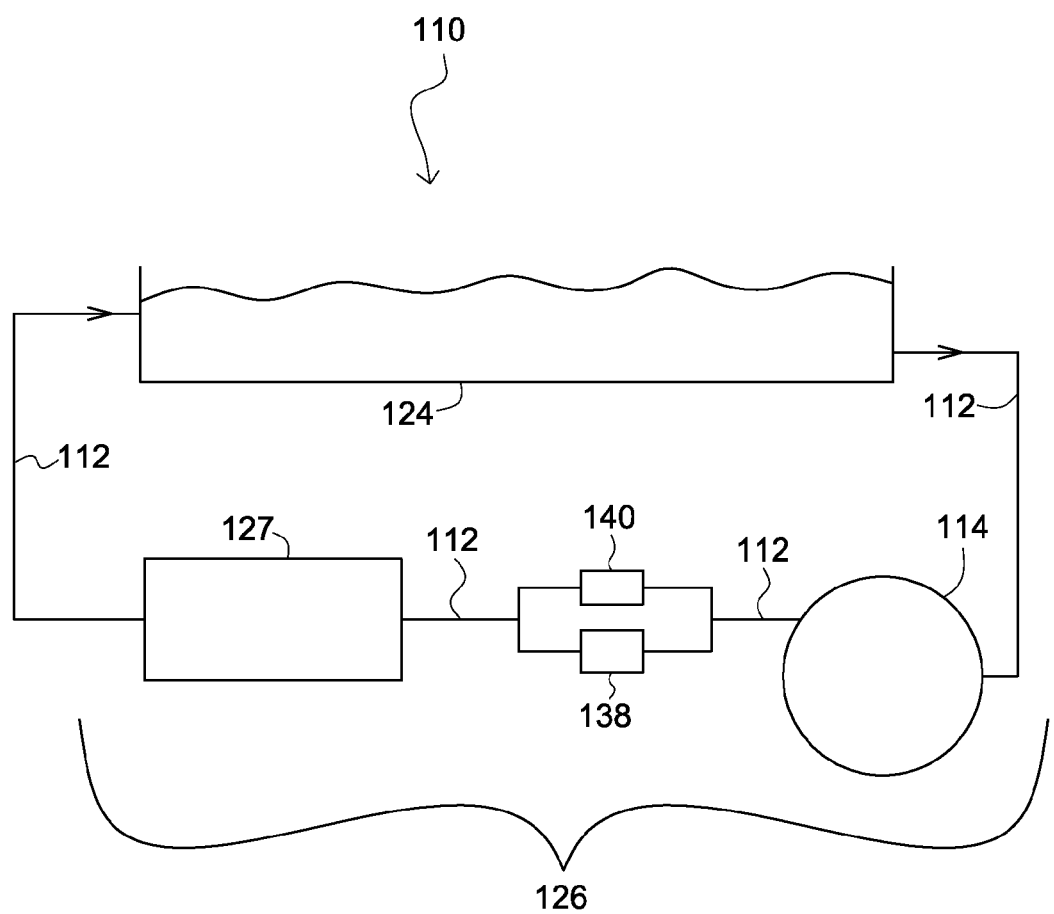
FIG. 1 is a schematic view of a water treatment device according to one embodiment of the present invention.

Embodiments of the present invention comprise water treatment devices that utilize UV radiation, magnetic field, and ozone fortified air to treat solute-laden water, highly alkaline water, and biologically contaminated water, or water that will likely become highly alkaline or biologically contaminated in the absence of treatment. An example of such water is cooling tower water. Other examples include, but are not limited to, oil or gas well by-product water and other contaminated water generated as a by-product of an industrial process or processes.

By use of the water treatment device, pH of solute laden water such as cooling tower water is modulated, and biologically contamination is highly controlled without the use of, or with substantially reduced use of, chemical agents. Water treatment costs are therefore reduced by use of the water treatment device over chemical treatment alone. Embodiments of the present invention effectively treat cooling tower water by preventing or eliminating biological contamination of the water, and by lowering pH about 0.2 units, or maintaining cooling tower water pH 0.2 units below what the pH would be if the cooling tower water were untreated.

The water treatment device mitigates total alkalinity such that alkalinity does not concentrate as fast as calcium ions, water hardness, chloride ions, conductivity, or other indices of cycles of concentration. In a typical installation, total alkalinity is 50%-75% of expected based on cycles of concentration indicated by increase in chloride ion concentration. The mechanism of action of the reduced alkalinity is not well understood; the fate of missing alkalinity is unknown. However, results of reduced alkalinity are highly beneficial, with deposition of scale and other mineral deposits on cooling tower parts being greatly reduced or eliminated completely.

In some embodiments, the water treatment device includes addition of glass media to water being treated, and subsequent filtration of the water. Such treatment removes or reduces suspended solids, including dead bacteria, and may help prevent infestation of water with Legionella bacteria.

Terminology

The terms and phrases as indicated in quotation marks (" ") in this section are intended to have the meaning ascribed to them in this Terminology section applied to them throughout this document, including in the claims, unless clearly indicated otherwise in context. Further, as applicable, the stated definitions are to apply, regardless of the word or phrase's case, to the singular and plural variations of the defined word or phrase.

The term "or" as used in this specification and the appended claims is not meant to be exclusive; rather the term is inclusive, meaning "either or both."

References in the specification to "one embodiment", "an embodiment", "another embodiment, "a preferred embodiment", "an alternative embodiment", "one variation", "a variation" and similar phrases mean that a particular feature, structure, or characteristic described in connection with the embodiment or variation, is included in at least an embodiment or variation of the invention. The phrase "in one embodiment", "in one variation" or similar phrases, as used in various places in the specification, are not necessarily meant to refer to the same embodiment or the same variation.

The term "couple" or "coupled" as used in this specification and appended claims refers to an indirect or direct connection between the identified elements, components, or objects. Often the manner of the coupling will be related specifically to the manner in which the two coupled elements interact.

The term "approximately," as used in this specification and appended claims, refers to plus or minus 10% of the value given. For example: "approximately 14.0 watts" means a range from 12.6 watts to 15.4 watts.

The term "about," as used in this specification and appended claims, refers to plus or minus 20% of the value given.

The terms "hyper-concentrated," and "solute laden," as used in this specification and appended claims, refers to circulating water (cooling tower water) that contains dissolved solids and other dissolved species at concentrations that are elevated at least 2 fold over feed water. For example, circulating water at a cycle of concentration of 2 is hyper-concentrated with dissolved solids.

The terms "biologically contaminated" and "biologically contaminated water," as used in this specification and appended claims, refers to circulating water (cooling tower water) with bacterial load of greater than 50,000 colonies per milliliter. It is recognized that 50,000 colonies per milliliter and higher is considered an acceptable level of bacterial contamination for circulating water under some water treatment schemes, and in the absence of effective water treatment, bacterial load in circulating water can reach 500,000 to 1,000,000 colonies per mL, or even higher. Bacterial load of 1000 colonies per milliliter and lower is achievable with embodiments of the water treatment device of the present invention.

The terms "polluted" or "polluted water" refers to water that is unfit for its intended use. Thus water that is intended to be used as drinking water may be polluted, but that same water could be acceptable, and therefore not polluted, if intended to be discharged into a river.

The term "oxygenated gas," as used in this specification and appended claims, refers to a gas phase mixture or solution comprising some form of oxygen at a level of at least 1% by weight. Forms of oxygen include monoatomic oxygen ($O_1$); diatomic oxygen, also known as ground state molecular oxygen ($O_2$); ozone or triatomic oxygen ($O_3$); diatomic oxygen with electrons in either of two excited states ($^1\Delta_g O_2$ and $^1\Sigma_g O_2$) known as singlet oxygen (either form of singlet oxygen represented here as $^1O_2$); and superoxide anion ($O_2^-$).

The term "air," as used in this specification and appended claims, refers to the commonly recognized gas that surrounds the surface of the earth and comprises approximately 78.08% $N_2$, 20.95% $O_2$, 0.934% Ar, and 0.0383% $CO_2$.

The term "oxygen supplemented air," as used in this specification and appended claims, refers to air comprising greater than 21.1% $O_2$ by weight.

The term "ozone fortified gas," as used in this specification and appended claims, refers to a gas comprising greater than 600 parts per billion ozone.

The term "ozone fortified air," as used in this specification and appended claims, refers to air comprising greater than 600 parts per billion ozone.

The term "ultraviolet radiation" or "UV radiation," as used in this specification and appended claims, refers to electromagnetic radiation having wavelength in a range from 40 nm to 400 nm. Accordingly, a UV radiation source emits electromagnetic radiation having wavelength in a range from 40 nm to 400 nm.

The term "substantially UV transmissive" or "substantially UV transmissive material," as used in this specification and appended claims, refers to material that transmits 50% or more of radiation having a wavelength of 254 nm, per 1 mm of material.

The term "substantially parallel," as used in this specification and appended claims, refers to lines or axes that are parallel plus or minus 3°.

A First Embodiment Water Treatment Device

A first embodiment water treatment device 126 is illustrated in FIGS. 1-4; none of FIGS. 1-4 are drawn to scale. A schematic representation of the first embodiment water treatment device 126 installed in a cooling tower water system 110 is illustrated in FIG. 1. The first embodiment water treatment device 126 comprises a radiation chamber 127, a gas injector 138, a valve 140, and a pump 114. The gas injector of the first embodiment water treatment device is a venturi. The cooling tower water system further comprises conduit 112 and a reservoir 124. The conduit serves to conduct water between the reservoir and the water treatment device, as well as to conduct water within the water treatment device. The reservoir of the cooling tower water system is a cooling tower basin, the cooling tower of which is paired to an air conditioner. A water treatment flow path proceeds clockwise from the reservoir 124 to the pump 114, then to either the valve 140 or the gas injector 138, before entering the radiation chamber 127 and finally returning to the reservoir 124. The water treatment flow path includes conduit 112 that travels between or through the other components disclosed above.

In operation, as illustrated in FIG. 1, water typically flows in a clockwise direction from the reservoir 124 to the pump 114, then to the gas injector 138. The reservoir serves as both a source of tainted water to be treated by the water treatment device 126 and as a destination for treated water. In some embodiments, treated water does not return to the source of the tainted water. Some embodiments use other sources of tainted water, such as tainted water from gas or oil wells.

In typical operation of the water treatment device 126, water flows through either the gas injector 138 or valve 140 before entering the radiation chamber 127. The gas injector (venturi) injects oxygenated gas into water that flows therethrough. Examples of oxygenated gas include, but are not limited to, air, oxygen supplemented air, relatively pure oxygen, ozone fortified air, and ozone fortified gas. Alternatively, water may flow through the valve 140, with volumes and proportions of water flowing through either the valve or the gas injector varying inversely, and water flow through the venturi thus being modulated by use of the valve. As is apparent to a person of ordinary skill in the art flow of water through the venturi is generally increased by closing or partially closing the valve. In some embodiments, the valve 140 is absent, and the proportion of water flow through the gas injector 138 is adjustable primarily through adjusting the flow rate of the pump 114. In some embodiments, the gas injector 138 is supplemented or supplanted by gas injection means other than the venturi. Gas injection means are adapted to inject gas into the flowing water, and include, but are not limited to, gas jets or nozzles adapted to inject gas under positive pressure into the water.

Water flows into the radiation chamber 127 where it is typically irradiated with UV radiation and subjected to a magnetic field. Treated water emerges from the radiation chamber whereupon it flows back to the reservoir 124. The radiation chamber 127 of the water treatment device 126 is illustrated in detail in a cross-section view in FIG. 2. The gas injector 138, which is a venturi, is also shown in greater detail in FIG. 2. The radiation chamber comprises a four inch diameter, thirty eight inch long UV resistant acrylonitrile butadiene styrene (ABS) plastic enclosure 128, within which is housed a UV radiation source 130, a magnetic rod 132, and a flow cell 142. The radiation chamber further comprises a bracket 154 in which is disposed an orifice 150 through which gas is relatively free to pass.

The magnetic rod 132 of the first embodiment is a copper tube within which reside six permanent magnets 134. Other embodiments may use electromagnets in place of or in addition to permanent magnets. The flow cell of the first embodiment water treatment device is a glass tube having an inside diameter of one inch and comprising UV quality quartz glass. The UV quality quartz glass of the first embodiment is GE Type 214 fused quartz (Momentive Performance Materials Quartz, Inc., Strongsville, Ohio), having UV radiation transmission of approximately 70% (per 1 mm material) at 185 nm and UV radiation transmission greater than 85% (per 1 mm material) at 254 nm. Other embodiments of water treatment devices include flow cells comprising substantially UV transmissive material. The flow cell 142 has a flow cell length 143 residing along a flow cell axis of cylinder, the flow cell length being approximately 30 inches. In other embodiments, the flow cell length is preferably at least 10 inches, more preferably at least 20 inches, and most preferably at least 30 inches. The flow cell is best adapted to irradiation along its flow cell length.

The UV radiation source 130 is a G36T5VH/4P ozone producing quartz UV lamp operating at approximately forty (40) watts power consumption, with a main spectral peak at approximately 253.7 nm and another spectral peak at approximately 185 nm. The G36T5VH/4P ozone producing quartz UV lamp is generally elongate and cylindrical, having a length of about 33 inches and a diameter of about 0.6 inches. It uses a universal B224PWUV-C ballast. The G36T5VH/4P lamp consumes approximately forty (40) watts power and emits approximately fourteen (14) watts power in the form of ultraviolet radiation. As is known to persons of ordinary skill in the art, radiation having a wavelength around 254 nm is highly antimicrobial. Similarly, radiation having a wavelength around 185 nm generates ozone in air, albeit inefficiently relative to corona discharge.

The flow cell 142 is coupled to the conduit 112 at conduit junctions 113, and cooling tower water flows through it during water treatment. Relatively high UV transparency of the quartz glass flow cell allows UV radiation to penetrate the flow cell to irradiate water contained therein. In the first embodiment, a distance between the UV radiation source and the flow cell is approximately 0.50 inch. In other embodiments, a distance between the UV radiation source and the flow cell is preferably between 0.1 and 12 inches, more preferably between 0.2 and 6 inches, and most preferably between 0.40 and 2.0 inches.

Figure 4:
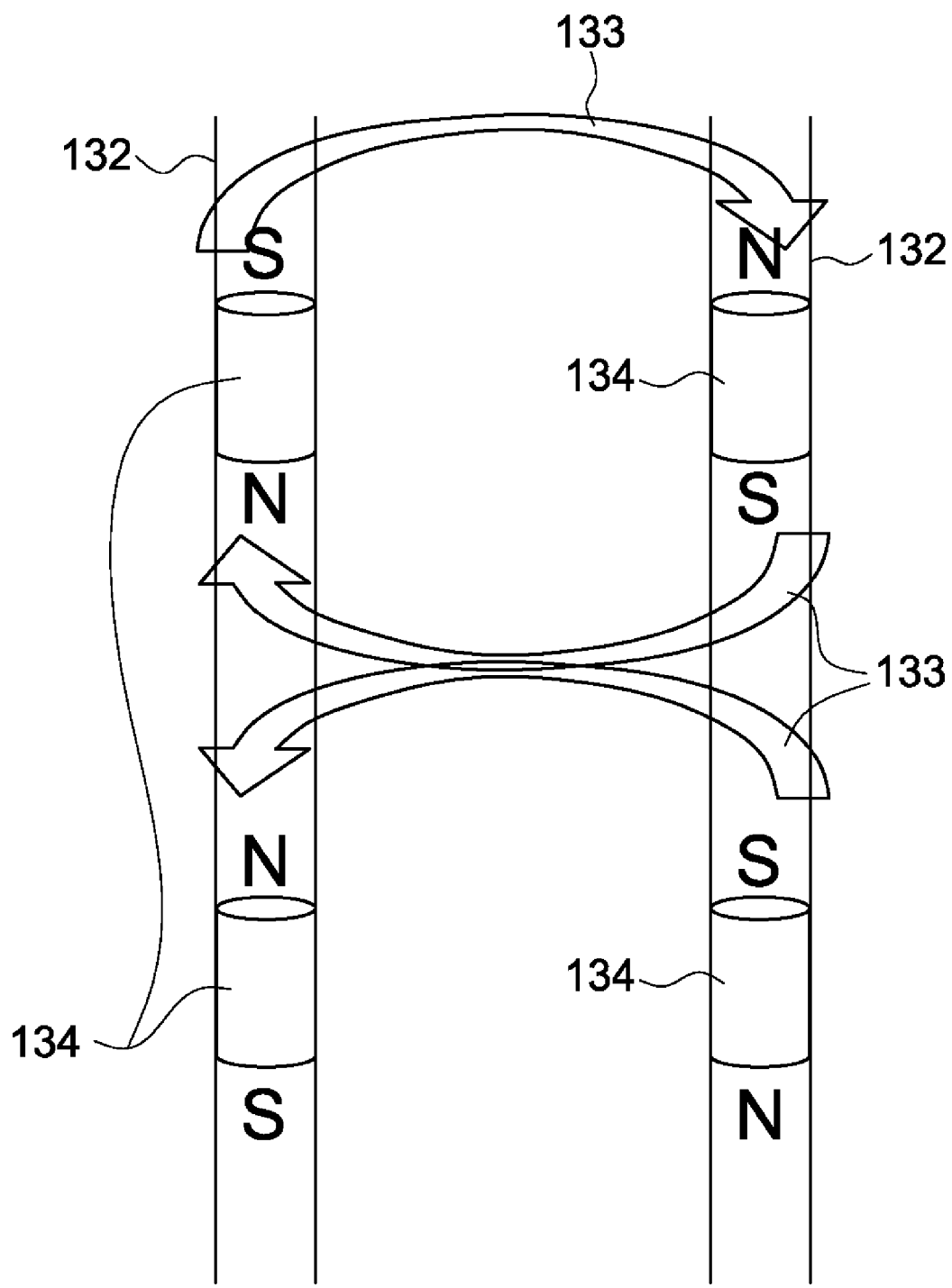
FIG. 4 is side view of a water treatment device according to one embodiment of the present invention.

The magnets 134 of the magnetic rod 132 are cylindrically shaped neodymium (Neodymium-Iron-Boron) grade N52, each magnet having a cylinder diameter of approximately 0.50 inch and a cylinder height of approximately 0.50 inch. The magnets are disposed in copper tubing having an inside diameter of approximately 0.50 inch, and are arranged with like poles of adjacent magnets oriented toward each other, as illustrated in FIG. 4. In the first embodiment, a distance between the magnetic rod and the flow cell is approximately 0.50 inch. In other embodiments, a distance between the magnetic rod and the flow cell is preferably between 0.1 and 12 inches, more preferably between 0.20 and 6 inches, and most preferably between 0.40 and 2.0 inches. In some embodiments, weaker permanent magnets are used. Electromagnets may also be used.

Figure 2:
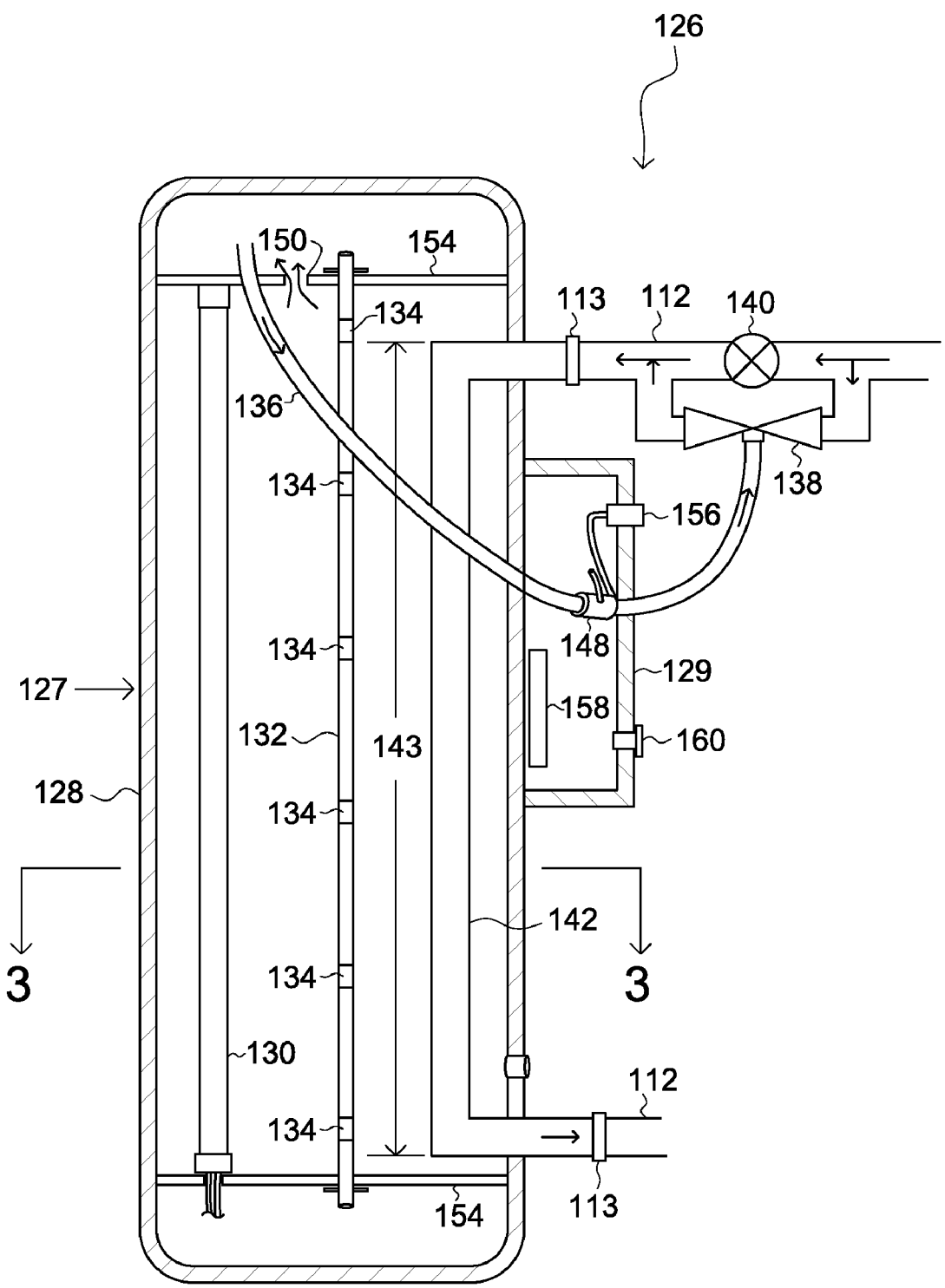
FIG. 2 is a side cross-section view of a water treatment device according to one embodiment of the present invention.

The first embodiment radiation chamber actually comprises two UV radiation sources (G36T5VH/4P ozone producing quartz UV lamps), two magnetic rods, and a single flow cell. In order to provide a simpler, less cluttered figure, only one UV radiation source 130 and one magnetic rod 132 are illustrated in FIG. 2. Similarly, as illustrated in FIG. 2, the magnetic rod 132 appears closer to the flow cell than does the UV radiation source. Orientation of the two UV radiation sources 130, two magnetic rods 132, and flow cell 142 inside the housing 128 of the radiation chamber 126 of the first embodiment water treatment device is better illustrated in FIG. 3, which illustrates a radial cross section of the radiation chamber.

Each of the flow cell 142, the UV radiation source 130, and the magnetic rod 132 are generally cylindrical, which means that each of the flow cell, UV radiation source, and magnetic rod have an axis of cylinder. As best illustrated in FIG. 2, the axes of cylinder for each of the flow cell, UV radiation source, and magnetic rod, are substantially parallel.

Radiation chambers typically comprise two G36T5VH/4P UV lamps, two magnetic rods, and a single one inch inside diameter flow cell, contained within an ABS plastic housing. A water treatment device comprising the single radiation chamber described above and a Mazzei #748 drawing one cubic foot per hour (CFH) ozone fortified air from within the radiation chamber is sufficient to effectively treat cooling tower water for up to 1000 tons of refrigeration, even where feed water quality is low. Low quality feed water typically has a pH value of 8.0 or greater and a hardness value of 200 ppm or greater. Additional radiation chambers can be added to increase capacity.

Water flow rate through the gas injector (venturi) 138 and flow cell 142 is typically about ten to twenty gallons per minute (GPM), which facilitates the venturi drawing a vacuum of about 15.0 inches Hg to about 25.0 inches Hg. Other embodiments comprise other UV radiation sources and magnets, and can operate effectively at other water flow rates.

UV radiation intensity and magnetic field strength in the flow cell impact the maximum water flow rate at which embodiments of the invention can treat water effectively. More powerful or more numerous magnets, or more UV radiation, allow embodiments of the water treatment device to operate effectively at higher water flow rates, or to treat "harder" water. Flow cell configuration can also be adapted to modulate exposure of flow cell contents to UV radiation. Accordingly, configuring the flow cell to increase flow cell contents exposure to UV radiation enables greater water flow rates for a UV radiation source of a given intensity. Similarly, decreasing distance between UV radiation sources and flow cells, or between magnets and flow cells, can result in higher flow rates that still result in effective water treatment.

The gas injector 138 of the first embodiment water treatment device is coupled to a gas feed tube 136, the gas feed tube being adapted to deliver air from inside the radiation chamber 127 to the gas injector, the radiation chamber air being introduced into water flowing at the gas injector. Because air in the radiation chamber is irradiated at about 185 nm, ozone is produced in the radiation chamber air. Thus, radiation chamber air that is introduced into flowing water at the gas injector is ozone fortified.

The gas injector 138 of the first embodiment water treatment device is a Mazzei #748 venturi, which creates air flow of one cubic foot per hour (CFH) when generating a vacuum of 15 inches Hg. In order to operate properly, the venturi of the first embodiment water treatment device draws a minimum vacuum of twelve inches Hg.

The first embodiment water treatment device further comprises a control panel 129 that houses (i) a ballast 158 (Universal # B224PWUV-C) to energize the UV lamp, (ii) a vacuum gauge 156, (iii) a vacuum test valve 148, and, (iv) a UV lamp ON/OFF switch 160.

Figure 3:
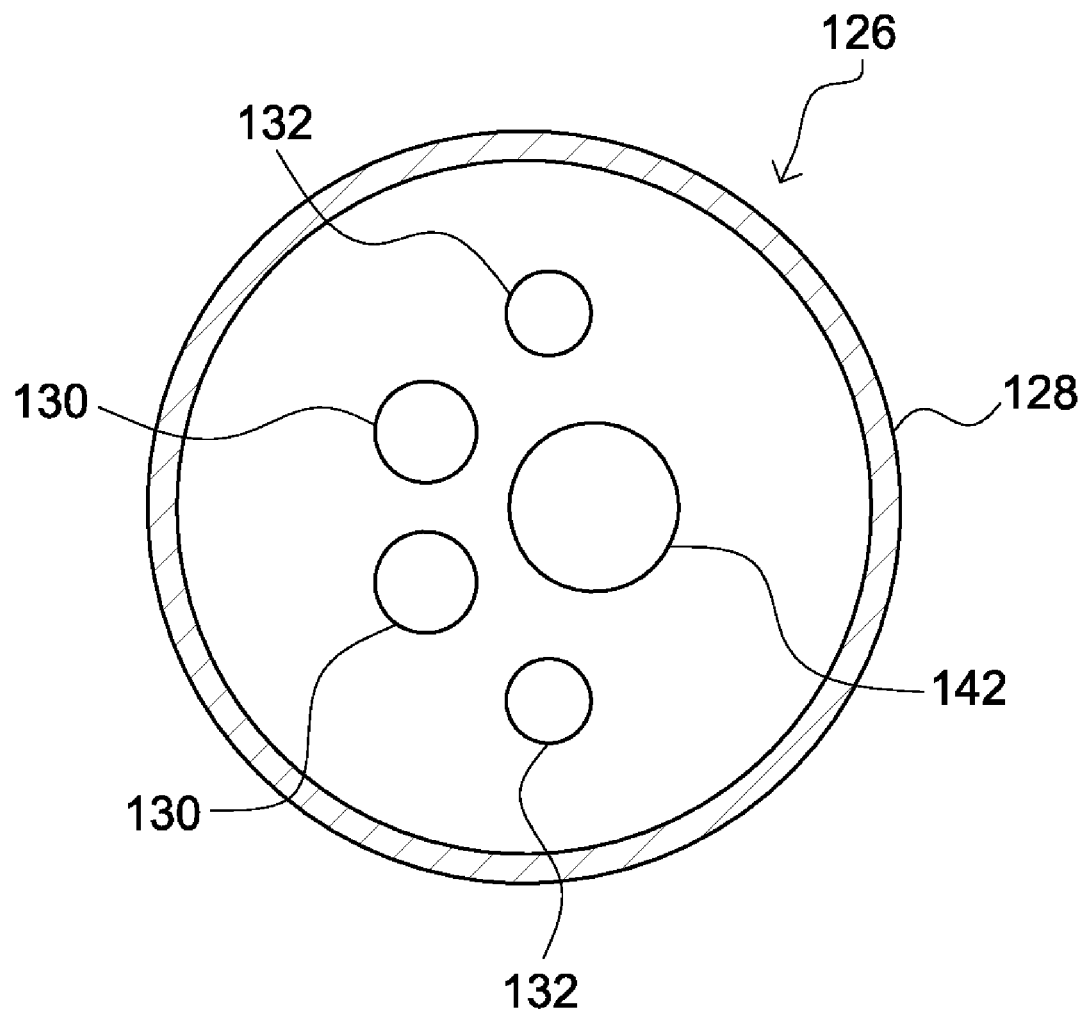
FIG. 3 is a top cross-section view of a water treatment device according to one embodiment of the present invention.

Typical orientation of two UV lamps 130 and two magnetic rods 132 containing neodymium magnets (not shown) is illustrated in FIG. 3. Orientation of four individual magnets 134 in two adjacent copper tubes 132 is illustrated in FIG. 4. As can be seen in FIG. 4, adjacent magnets within one copper tube are oriented with like poles closest to each other. This orientation generates desirable magnetic field orientations, indicated by magnetic field arrows 233.

Cooling Tower Water Treated Using Embodiments of Water Treatment Devices

Examples of cooling tower water during treatment with embodiments of water treatment devices according to the present invention are shown in Table I. Each of the water treatment devices whose results are summarized in Table I is substantially similar and comprises: two G36T5VH/4P ozone producing quartz UV lamps; two magnetic rods, each magnetic rod comprising six neodymium grade N52 magnets, each magnet being cylindrical and approximately ½ inch diameter by ½ inch long and installed inside ½ inch inside diameter copper tubes; one flow cell comprising an approximately 1 inch inside diameter quartz glass (GE Type 214 fused quartz) tube approximately 30 inches long; and one Mazzei #748 venturi. The water treatment devices are configured as shown in FIGS. 1-4, with the UV lamps, magnetic rods, and flow cell enclosed in a radiation chamber housing, and the venturi drawing ozone fortified air from within the radiation chamber. The venturi vacuum is maintained at 15 inches to 25 inches Hg, such that the venturi draws approximately 1.0 CFH gas or more from within the reaction chamber. The magnets are oriented in the magnetic rods as shown in FIG. 4.

TABLE I

| FACILITY[A] | SAMPLE[B] SOURCE | COND.[C] | CHLORIDE (ppm) | C of C[D] (chloride) | ALK.[E] (ppm) | C of C[F] (ALK.) | % ALK.[G] |
|---|---|---|---|---|---|---|---|
| A - 400 | Feed water | 1054 | 90 | — | 90 | — | — |
| TONS | Tower water | 4110 | 330 | 3.66 | 200 | 2.22 | 60% |
| B - 540 | Feed water | 930 | 55 | — | 200 | — | |
| TONS | Tower water | 3129 | 220 | 4.0 | 400 | 2.00 | 50% |
| C - 500 | Feed water | 442 | 54 | — | 100 | | |
| TONS | Tower water | 2207 | 284 | 5.26 | 386 | 3.86 | 73% |
| D - 600 | Feed water | 277 | 29 | — | 84 | | |
| TONS | Tower water | 1870 | 213 | 7.34 | 344 | 4.10 | 56% |
| E - 1300 | Feed water | 281 | 25 | — | 74 | | |
| TONS | Tower water | 1663 | 181 | 7.24 | 360 | 4.86 | 67% |

[A] Facilities A-E are cooling towers located in California and Colorado, the cooling towers serving refrigeration/air conditioning units having cooling capacity listed. One ton of cooling capacity=removal of 12000 BTU per hour.

[B] The source of each sample is either tower water, which is concentrated by evaporation that occurs during normal cooling tower operation, or feed water, which is the source for all water in the cooling tower.

[C] COND.=conductivity in microSiemens. Conductivity is a function of ionic species dissolve in the water.

[D] C of C (chloride)=cycles of concentration as calculated using chloride ion concentration. By definition, cycles of concentration of feed water=one. Cycles of concentration of tower water is calculated by dividing tower water chloride concentration by feed water chloride concentration. Chloride ion concentration is used here to calculate cycles of concentration because chloride ion does not evaporate and is unaffected by the water treatment device.

[E] Alkalinity is reported in ppm (mg/L) $CaCO_3$.

[F] C of C (alk.)=cycles of concentration as calculated using alkalinity.

[G] % alkalinity is cycles of concentration as calculated using alkalinity, divided by cycles of concentration using chloride. The cycles of concentration using chloride is used here as an index of actual cycles of concentration of cooling tower water.

As shown in Table I, treatment of tower water with the water treatment device results in less alkalinity than would be predicted based on cycles of concentration calculated using chloride ion. Percent alkalinity ranges from 50% to 73% of predicted, the predicted value being based on cycles of concentration calculated using chloride. For instance, for Facility A, a cooling tower servicing a refrigeration unit having 400 tons of cooling capacity, chloride concentration indicates that tower water is 3.66 times as concentrated as feed water (cycles of concentration based on chloride=3.66). Accordingly, one would expect to find total alkalinity in tower water also increased 3.66 times over feed water. As measured, however, alkalinity is actually increased only 2.22 times, approximately 60% of the predicted value. This 40% reduction in alkalinity has beneficial effects of permitting cooling tower water to be run at higher cycles of concentration, while minimizing scale and other deposition of solids on cooling tower components. Less water use and cleaner cooling tower components are thus beneficial consequences of the reduced alkalinity. The mechanism of action for reduced alkalinity is not well understood, but is a consequence of treating cooling tower water with the water treatment device.

Alternative Embodiments and Variations

The various embodiments and variations thereof, illustrated in the accompanying Figures and/or described above, are merely exemplary and are not meant to limit the scope of the invention. It is to be appreciated that numerous other variations of the invention have been contemplated, as would be obvious to one of ordinary skill in the art, given the benefit of this disclosure. All variations of the invention that read upon appended claims are intended and contemplated to be within the scope of the invention.

I claim:

1. A water treatment device comprising:
a radiation chamber, the radiation chamber including a housing within which resides (i) a radiation source, wherein the radiation source emits radiation having a wavelength of approximately 254 nm and radiation having a wavelength of approximately 185 nm, and wherein the radiation source is generally cylindrical and has a first axis of cylinder, (ii) a magnetic field source, the magnetic field source comprising electromagnets or permanent magnets included in at least a first magnetic rod, wherein the at least first magnetic rod is generally cylindrical and has a second axis of cylinder, and (iii) a flow cell, the flow cell comprising a substantially UV transmissive material, wherein the flow cell is generally cylindrical and has a third axis of cylinder, and wherein the first, second and third axes of cylinder of the radiation source, the at least first magnetic rod, and the flow cell respectively are separate from and substantially parallel to one another, and wherein each of the radiation source, the first magnetic rod, and the flow cell are substantially surrounded by air within the radiation chamber;
a water flow path, the water flow path including the flow cell and being adapted to contain a flow of water, wherein at least most of the water flow path through the radiation chamber is defined by the flow cell; and
a gas injector, the gas injector being adapted to inject a gas from the radiation chamber into the water flow path.

2. The water treatment device of claim 1, wherein:
the radiation source comprises a UV lamp, the UV lamp being adapted to emit ultraviolet radiation in a quantity of approximately 14 watts or more;
the flow cell is disposed within 12 inches of the radiation source;
the magnetic field source is disposed within 12 inches of the radiation source; and
the gas injector is a venturi, the venturi being adapted to draw the gas from within the housing when the venturi is drawing a vacuum.

3. The water treatment device of claim 2, wherein:
the radiation source comprises two UV lamps, each of the two UV lamps being adapted to emit ultraviolet radiation in a quantity of approximately 14 watts or more.

4. The water treatment device of claim 3, wherein:
the flow cell comprises a flow cell axis of cylinder and has a length dimension of at least 10 inches, the length dimension being along the flow cell axis of cylinder;
each of the two UV lamps comprises a lamp axis of cylinder; and
the flow cell axis of cylinder and both of the lamp axes of cylinder are substantially parallel.

5. The water treatment device of claim 4, wherein:
the each of the two UV lamps comprises a length dimension that resides along the lamp axis of cylinder, the length dimension of each of the each of the two UV lamps being at least 30 inches; and
the flow cell length dimension is at least about 30 inches.

6. The water treatment device of claim 5, wherein the magnetic field source comprises a neodymium magnet having a grade of at least N40.

7. The water treatment device of claim 6, wherein the neodymium magnet comprises two or more individual magnets, two of the two or more individual magnets being oriented such that a straight line through a center of mass of the two of the two or more individual magnets is substantially parallel to the flow cell axis of cylinder.

8. The water treatment device of claim 7, wherein the two of the two or more individual magnets are oriented with one set of like poles facing each other, and no other magnet residing directly in between the two of the two or more individual magnets.

9. A cooling tower water system comprising:
a cooling tower, the cooling tower comprising cooling tower water;
the water treatment device of claim 4, wherein the water treatment device is functionally coupled to the cooling tower to treat the cooling tower water.

10. A cooling tower water system comprising:
a cooling tower, the cooling tower comprising cooling tower water;
the water treatment device of claim 5, wherein the water treatment device is functionally coupled to the cooling tower to treat the cooling tower water.

11. The water treatment device of claim 1, wherein the water flow path includes a conduit, wherein a first section of the conduit passes through a wall of the radiation chamber and supplies water to the flow cell, wherein the first section of the conduit is connected to the flow cell via a first conduit junction, wherein a second section of the conduit passes through the wall of the radiation chamber and receives water from the flow cell, wherein the second section of conduit is connected to the flow cell by a second conduit junction, and wherein at the first and second conduit junctions the first and second conduits are parallel to one another and at a right angle to the flow cell.

12. A method of treating cooling tower water comprising:
pumping water from a cooling tower into a water treatment device wherein the water treatment device includes:
a radiation chamber, the radiation chamber including a housing within which resides (i) a radiation source, wherein the radiation source is generally cylindrical and has a first axis of cylinder, (ii) a magnetic field source, the magnetic field source comprising electromagnets or permanent magnets included in a magnetic rod, wherein the magnetic rod is generally cylindrical and has a second axis of cylinder, and (iii) a flow cell, the flow cell comprising substantially UV transmissive material, wherein the flow cell is generally cylindrical and has a third axis of cylinder, and wherein the first, second and third axes of cylinder of the radiation source, the magnetic rod, and the flow cell respectively are separate from and are substantially parallel to one another, and wherein each of the radiation source, the magnetic rod, and the flow cell are substantially surrounded by air within the radiation chamber;

a water flow path, the water flow path including the flow cell and being adapted to contain a flow of water, wherein the water flow path through the radiation chamber is at least partially defined by the flow cell;

at least some of the water from the cooling tower flowing along the water flow path through a venturi and through the flow cell;

each of the two UV lamps comprising the radiation source emitting ultraviolet radiation in an amount of approximately 14 watts or more;

drawing air from within the housing into the venturi and into the water flowing through the venturi.

13. The method of treating cooling tower water of claim 12, wherein the air is ozone fortified air.

14. The method of treating cooling tower water of claim 13, wherein the ozone fortified air is drawn into the venturi at a rate of 0.50 CFR or more.

15. The method of treating cooling tower water of claim 14, wherein the flow cell has an inside diameter of approximately 1.0 inch, and the flow cell comprises quartz glass having transmittance of at least 80% at 254 nm, per 1 mm glass.

16. The method of treating cooling tower water of claim 15, wherein the water is pumped through the flow cell at approximately 10 GPM to approximately 20 GPM.

17. The method of treating cooling tower water of claim 12, wherein prior to drawing air from within the radiation chamber housing into the venturi and into the water flowing through the venturi the air is drawn past the two UV lamps and the flow cell.

18. A water treatment device comprising:
a radiation chamber, the radiation chamber including:
a housing, the housing being substantially opaque to UV radiation and substantially enclosing other radiation chamber components;
two UV lamps, the two UV lamps residing within the housing and each of the two UV lamps being adapted to emit approximately 14 watts or more UV radiation, wherein the two UV lamps are generally cylindrical and lie along substantially parallel axes;
a flow cell; the flow cell (i) having a length of at least 20 inches; (ii) residing within approximately 2.0 inches of at least one of the two UV lamps for most of its length; and (iii) comprising substantially UV transmissive glass, wherein the flow cell is generally cylindrical and lies along an axes that is substantially parallel to and separate from the axes of the UV lamps;
a magnetic field source, the magnetic field source residing within the housing and comprising permanent magnets or electromagnets, wherein the magnetic field source includes a plurality of magnets arranged along an axis that is substantially parallel to and separate from the UV lamp axes and the flow cell axis;
a venturi;
a gas line, the gas line running from inside the radiation chamber to the venturi and being adapted to carry a gas from inside the radiation chamber to the venturi.

19. The water treatment device of claim 18, wherein at least one of the two UV lamps has a main spectral peak at approximately 254 nm, and at least one of the two UV lamps has a spectral peak at approximately 185 nm.

20. A method of treating cooling tower water comprising:
water flowing from a cooling tower into a water treatment device, the water treatment device including:
a radiation chamber, the radiation chamber including:
a housing, the housing being substantially opaque to UV radiation and substantially enclosing other radiation chamber components;
two UV lamps, the two UV lamps residing within the housing, wherein the two UV lamps are generally cylindrical and lie along substantially parallel axes;
a flow cell, the flow cell comprising substantially UV transmissive glass, wherein the flow cell is generally cylindrical and lies along an axes that is substantially parallel to and separate from the axis of the UV lamps;
a magnetic field source, the magnetic field source residing within the housing and comprising permanent magnets or electromagnets, wherein the magnetic field source includes a plurality of magnets arranged along an axis that is substantially parallel to and separate from the UV lamp axes and the flow cell axis;
a venturi;
a gas line, the gas line running from inside the radiation chamber to the venturi and being adapted to carry a gas from inside the radiation chamber to the venturi; water flowing through the venturi and the flow cell;
the each of the two UV lamps emitting more than approximately 14 watts of UV radiation;
ozone fortified air flowing from inside the radiation chamber to the venturi.

21. The method of treating cooling tower water of claim 20, further comprising the venturi dispensing at least 0.50 CFR ozone fortified air into the cooling tower water.

22. The method of treating cooling tower water of claim 21, wherein the magnetic field source comprises at least 6 individual N52 grade neodymium magnets.

* * * * *